(12) United States Patent
Wang

(10) Patent No.: US 12,370,336 B2
(45) Date of Patent: Jul. 29, 2025

(54) RESPIRATORY MONITOR DEVICE AND RESPIRATORY MONITORING SYSTEM

(71) Applicant: BOE TECHNOLOGY GROUP CO., LTD., Beijing (CN)

(72) Inventor: Qiang Wang, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 967 days.

(21) Appl. No.: 17/298,170

(22) PCT Filed: Aug. 19, 2020

(86) PCT No.: PCT/CN2020/110032
§ 371 (c)(1),
(2) Date: May 28, 2021

(87) PCT Pub. No.: WO2021/036885
PCT Pub. Date: Mar. 4, 2021

(65) Prior Publication Data
US 2022/0111172 A1 Apr. 14, 2022

(30) Foreign Application Priority Data
Aug. 23, 2019 (CN) .......................... 201921391002.2

(51) Int. Cl.
*A61M 16/08* (2006.01)
*A61M 16/00* (2006.01)
*A61M 16/10* (2006.01)

(52) U.S. Cl.
CPC .... *A61M 16/0841* (2014.02); *A61M 16/0003* (2014.02); *A61M 16/0816* (2013.01); *A61M 16/1005* (2014.02); *A61M 2016/0027* (2013.01)

(58) Field of Classification Search
CPC .............. A61M 16/08; A61M 16/0816; A61M 16/0841; A61M 16/085; A61M 16/0858;
(Continued)

(56) References Cited

U.S. PATENT DOCUMENTS

| 5,178,155 A | 1/1993 | Mault |
| 5,494,071 A * | 2/1996 | Bell ..................... G01L 19/0007 |
| | | 137/884 |

(Continued)

FOREIGN PATENT DOCUMENTS

| CN | 101547716 A | 9/2009 |
| CN | 101677783 A | 3/2010 |

(Continued)

OTHER PUBLICATIONS

Extended European search report of counterpart European application No. 20855959.1 issued on Aug. 19, 2022.

*Primary Examiner* — Kendra D Carter
*Assistant Examiner* — Jaeick Jang
(74) *Attorney, Agent, or Firm* — Lippes Mathias LLP

(57) ABSTRACT

Provided is a respiratory monitor device, relating to the field of medical devices. The respiratory monitor device comprises an external pipe and a monitor, and the external tubing is detachably connected to the monitor; the external tubing is provided with an air inlet and an air outlet, the air inlet is communicated with the air outlet by means of a cavity of the external tubing, and the external tubing comprises a plurality of first through holes; the monitor comprises a plurality of second through holes, the plurality of first through holes and the plurality of second through holes are communicated in one-to-one correspondence when the external tubing and the monitor are connected, and the monitor is used for detecting gas entering the monitor from the through holes.

14 Claims, 8 Drawing Sheets

(58) Field of Classification Search
CPC .......... A61M 16/0003; A61M 16/0006; A61M 16/0009; A61M 16/0012; A61M 16/10; A61M 16/1005; A61M 2016/102; A61M 2016/1025; A61M 2016/103; A61M 2016/1035; A61M 2016/0027; A61M 2016/003; A61M 2016/0033; A61M 2016/0036; A61M 2016/0039; A61M 2016/0042; A61B 5/08; A61B 5/087; A61B 5/091; G01F 1/34; G01F 1/36; G01F 1/44; G01F 1/40; G01F 1/46; G01F 1/42; G01F 1/6847

See application file for complete search history.

(56) References Cited

U.S. PATENT DOCUMENTS

| | | | |
|---|---|---|---|
| 5,925,831 | A | 7/1999 | Storsved |
| 6,126,610 | A | 10/2000 | Rich et al. |
| 10,441,196 | B2 * | 10/2019 | Eckerbom ......... A61M 16/0672 |
| 2007/0107728 | A1 | 5/2007 | Ricciardelli et al. |
| 2009/0020120 | A1 | 1/2009 | Schatzl et al. |
| 2010/0106040 | A1 | 4/2010 | Orr et al. |
| 2010/0168599 | A1 | 7/2010 | Esposito et al. |
| 2016/0287139 | A1 * | 10/2016 | Luttrell ............. A61M 16/0006 |

FOREIGN PATENT DOCUMENTS

| | | | | |
|---|---|---|---|---|
| CN | 107174250 A | * | 9/2017 | ............. A61B 5/091 |
| CN | 211213155 U | | 8/2020 | |
| WO | WO-2004001272 A1 | * | 12/2003 | ............. A61M 1/10 |
| WO | WO-2013098731 A1 | * | 7/2013 | ............. A61B 5/087 |
| WO | 2016156176 A1 | | 10/2016 | |
| WO | 2016161036 A1 | | 10/2016 | |

\* cited by examiner

RESPIRATORY MONITOR DEVICE AND RESPIRATORY MONITORING SYSTEM

This application is a 371 of PCT Application No. PCT/CN2020/110032, filed on Aug. 19, 2020, which claims priority to Chinese Patent Application No. 201921391002.2, filed on Aug. 23, 2019 and entitled "RESPIRATORY MONITOR AND RESPIRATORY MONITORING SYSTEM," the disclosure of which is incorporated herein by reference in its entirety.

TECHNICAL FIELD

The present disclosure relates to the field of medical instruments, and in particular, relates to a respiratory monitor device and a respiratory monitoring system.

BACKGROUND

For users who need a respiratory monitor device to facilitate normal respiration, sanitation of the respiratory monitor device is very important.

The respiratory monitor device includes an external tubing and a monitor. The external tubing is configured to provide a gas path for supplying oxygen to the user, and the external tubing is in direct contact with the user. The monitor includes a circuit structure configured to monitor information such as a flow rate of oxygen circulating in the external tubing. In order to ensure the sanitation, the external tubing needs to be cleaned in time.

SUMMARY

Embodiments of the present disclosure provide a respiratory monitor device and a respiratory monitoring system. The embodiments of the present disclosure adopt the following technical solution.

In one aspect, the embodiments of the present disclosure provide a respiratory monitor device including an external tubing and a monitor, wherein the external tubing and the monitor are detachably connected;

the external tubing is provided with a gas inlet and a gas outlet, wherein the gas inlet is in communication with the gas outlet by a chamber of the external tubing, and the external tubing includes a plurality of first through holes; and the monitor includes a plurality of second through holes, wherein when the external tubing is connected to the monitor, the plurality of first through holes are in communication with the plurality of second through holes in one-to-one correspondence, and the monitor is configured to detect gas entering the monitor from the second through holes.

Optionally, the external tubing and the monitor are each provided with a connecting surface, wherein one of the connecting surfaces of the external tubing and the monitor has a clamping slot, the other connecting surface has a protrusion matching the clamping slot, and the external tubing and the monitor are detachably connected by the clamping slot and the protrusion.

Optionally, one of the connecting surfaces of the external tubing and the monitor is provided with a plurality of clamping slots arranged in an array, the other connecting surface is provided with a plurality of protrusions which are arranged in an array and match the plurality of clamping slots respectively, and the external tubing and the monitor are detachably connected by the plurality of protrusions and the plurality of clamping slots.

Optionally, the clamping slot is a rectangular slot, and the protrusion is a rectangular protrusion.

Optionally, the clamping slot is a circular slot, and the protrusion is a circular protrusion.

Optionally, the plurality of first through holes and the plurality of second through holes are connected by a pluggable connecting tube.

Optionally, the external tubing is provided with a first annular protrusion surrounding the first through hole, and the monitor is provided with a second annular protrusion surrounding the second through hole, wherein when the external tubing is connected to the monitor, a first end of the connecting tube sleeves the first annular protrusion, a second end of the connecting tube sleeves the second annular protrusion, and the first through hole is in communication with the second through hole by a tube body of the connecting tube.

Optionally, the external tubing and the monitor are each provided with a connecting surface, and the respiratory monitor device further includes a sealing member, wherein when the external tubing is connected to the monitor, the connecting surface of the external tubing and the connecting surface of the monitor are sealed by the sealing member.

Optionally, a first annular slot surrounding the first through hole is disposed in the connecting surface of the external tubing, wherein the sealing member is embedded in the first annular slot, and a thickness of the sealing member is greater than or equal to a slot depth of the first annular slot.

Optionally, a first annular slot surrounding the first through hole is disposed in the connecting surface of the external tubing, and the sealing member is embedded in the first annular slot; and the connecting surface of the monitor is provided with a third annular protrusion surrounding the second through hole, wherein the third annular protrusion matches the second annular slot in shape, and a sum of a height of the third annular protrusion and the thickness of the sealing member is greater than or equal to the slot depth of the first annular slot.

Optionally, a second annular slot surrounding the second through hole is disposed in the connecting surface of the monitor, wherein the sealing member is embedded in the second annular slot, and the thickness of the sealing member is greater than or equal to the slot depth of the second annular slot.

Optionally, a second annular slot surrounding the second through hole is disposed in the connecting surface of the monitor, wherein the sealing member is embedded in the second annular slot; and a fourth annular protrusion surrounding the first through hole is disposed on the connecting surface of the external tubing, wherein the fourth annular protrusion matches the second annular slot in shape, and a sum of a height of the fourth annular protrusion and the thickness of the sealing member is greater than or equal to the slot depth of the second annular slot.

Optionally, a third annular slot surrounding the second through hole is disposed in the connecting surface of the monitor; and the connecting surface of the external tubing is provided with a fourth annular slot surrounding the first through hole, wherein the sealing member is embedded in at least one of the third annular slot and the fourth annular slot, and the thickness of the sealing member is greater than or equal to a sum of slot depths of the third annular slot and the fourth annular slot.

Optionally, the sealing member is made of a deformable material.

Optionally, the sealing member is a sealing ring.

Optionally, the plurality of first through holes are sequentially arranged along a direction from the gas inlet to the gas outlet.

Optionally, the number of second through holes is at least three;

the monitor includes at least one pressure sensor and at least one differential pressure sensor; wherein in the at least three second through holes, one ends of two adjacent second through holes going distally from the external tubing are both in direct contact with the differential pressure sensor, the differential pressure sensor is configured to acquire the difference between pressure intensities of the gas entering the monitor from the two adjacent second through holes, one end of any one second through holes of the remaining second through holes going distally from the external tubing is in direct contact with one of the pressure sensors, and the pressure sensor is configured to acquire the pressure intensity of the gas entering the monitor from any one second through hole of the remaining second through holes.

Optionally, the respiratory monitor device further includes a locking switch, wherein the locking switch is configured to fixedly connect the monitor and the external tubing.

Optionally, the locking switch is one of a snap switch and an electromagnetic switch.

In another aspect, the embodiments of the present disclosure further provide a respiratory monitoring system. The respiratory monitoring system includes an oxygen generator and any respiratory monitor device in the above embodiment; wherein an oxygen outlet of the oxygen generator is configured to be fixedly connected to the gas inlet of the respiratory monitor device.

DETAILED DESCRIPTION

Figure 1:
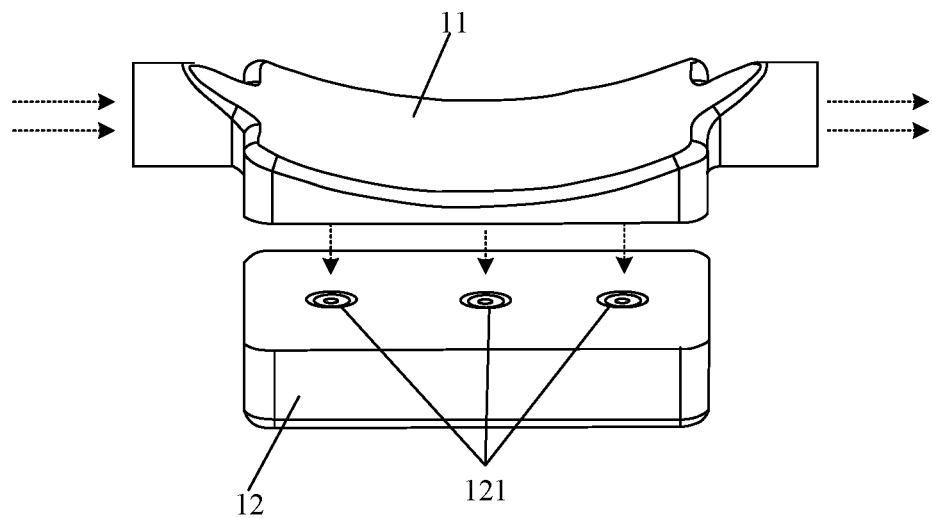
FIG. 1 is a schematic structural diagram of a respiratory monitor device according to an embodiment of the present disclosure.
Figure 2:
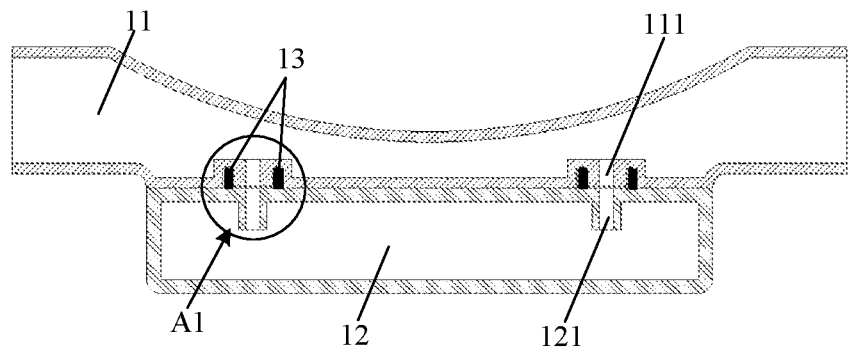
FIG. 2 is a schematic cross-sectional view of a respiratory monitor device according to an embodiment of the present disclosure.

The technical solutions according to the present disclosure are clearly and completely described hereinafter with reference to the accompanying drawings and the embodiments of the present disclosure. It is obvious that the described embodiments are only part but not all of the embodiments of the present disclosure. All other embodiments obtained by those skilled in the art without creative efforts based on the embodiments in the present disclosure are within the protection scope of the present disclosure.

An embodiment of the present disclosure provides a respiratory monitor device. As shown in FIG. 1 to FIG. 7, the respiratory monitor device includes an external tubing 11 and a monitor 12. The external tubing 11 and the monitor 12 are detachably connected. That is, whether the external tubing 11 and the monitor 12 are in a separated state or in an aligned state may be selected according to application requirements.

The external tubing 11 has a gas inlet and a gas outlet. The gas inlet is in communication with the gas outlet by a chamber of the external tubing 11. The external tubing 11 includes a plurality of first through holes 111 not shown in FIG. 1. The gas inlet may be connected to an external instrument, and the gas outlet may be in direct contact with the user. For example, the gas inlet may be connected to an oxygen generator, which is configured to provide oxygen to the respiratory monitor device.

The monitor 12 includes a plurality of second through holes 121. When the external tubing 11 is connected to the monitor 12, the plurality of first through holes 111 are in communication with the plurality of second through holes 121 in one-to-one correspondence. The monitor 12 is configured to detect the gas entering the monitor 12 from the second through holes 121.

Gas such as oxygen or air may enter the external tubing 11 by the gas inlet. A part of the gas flows out from the gas outlet and provides the oxygen to the user, and the other part of the gas flows into the monitor 12 by the first through hole 111 and the second through hole 121. The monitor 12 monitors a flow rate of the gas. The dotted arrow in FIG. 1 indicates a flow path of the oxygen.

Exhaled gas of the user may also enter the external tubing 11 from the gas outlet. A part of the exhaled gas flows out from the gas inlet, and the other part of the exhaled gas flows into the monitor 12 by the first through hole 111 and the second through hole 121. The monitor 12 monitors the flow rate of the exhaled gas to monitor a respiratory condition of the user.

Moreover, when the external tubing 11 includes a plurality of first through holes 111, the gas circulating in the external tubing 11 may enter the monitor 12 from different first through holes 111.

In summary, in the respiratory monitor device according to the embodiment of the present disclosure, since the monitor is detachably connected to the external tubing, when the external tubing needs to be cleaned, the external tubing can be detached from the respiratory monitor device, and the external tubing is cleaned separately to avoid damage to the monitor during cleaning since the external tubing and the monitor cannot be detached.

In the embodiment of the present disclosure, the shapes of the first through hole 111 and the second through hole 121 are not limited as long as the first through hole 111 is butt-jointed to and in communication with the second through hole 121. In an example, the end opening of one end of the first through hole 111 to be butt-jointed with the second through hole 121, and the end opening of one end of the second through hole 121 to be butt-jointed with the first through hole 111 may be correspondingly the same in shape and size.

As a first practice of detachable connection between the external tubing 11 and the monitor 12, both the external tubing 11 and the monitor 12 have a connecting surface. One of the connecting surfaces of the external tubing 11 and the monitor 12 has a clamping slot, and the other connecting surface has a protrusion matching the clamping slot. The external tubing 11 and the monitor 12 are detachably connected by the clamping slot and the protrusion. That is, when the clamping slot and the protrusion are connected in a clamping manner, the external tubing 11 and the monitor 12 are in the connected state. When the clamping slot and the protrusion are not connected in a clamping manner, the external tubing 11 and the monitor 12 are in the separated state.

As a second practice of the detachable connection between the external tubing 11 and the monitor 12, both the external tubing 11 and the monitor 12 have a connecting surface. One of the connecting surfaces of the external tubing 11 and the monitor 12 has a plurality of clamping slots arranged in an array. The other connecting surface has a plurality of protrusions which are arranged in an array and match the plurality of multiple clamping slots respectively. The external tubing 11 and the monitor 12 are detachably connected by the plurality of protrusions and the plurality of clamping slots. That is, when the plurality of clamping slots and the plurality of protrusions are connected in a manner of clamping and one-to-one correspondence, the external tubing 11 and the monitor 12 are in the connected state. When the plurality of clamping slots and the plurality of protrusions are not connected in a clamping manner, the external tubing 11 and the monitor 12 are in the separated state.

Optionally, the arrangement of the plurality of clamping slots and the plurality of protrusion arrays may be circular arrangement, or linear arrangement. In this way, on one hand, the insertion and removal of the clamping slot and the protrusion are facilitated. On the other hand, the effective fixing of the clamping slot and the protrusion can be realized to ensure the connecting stability of the external tubing 11 and the monitor 12.

Moreover, in the first and second practice, the shapes of the clamping slot and the protrusion may be selected according to application requirements, which is not specifically limited by the embodiment of the present disclosure. For example, the clamping slot may be a rectangular slot, and the protrusion may be a rectangular protrusion matching the rectangular slot. For another example, the clamping slot is a circular slot, and the protrusion may be a circular protrusion matching the circular slot.

As a third practice of the detachable connection between the external tubing 11 and the monitor 12, the plurality of first through holes 111 and the plurality of second through holes 121 may be connected by a pluggable connecting tube. That is, when the external tubing 11 needs to be fixedly connected to the monitor 12, a first end of the connecting tube may be fixedly connected to the external tubing 11, and a second end of the connecting tube may be fixedly connected to the monitor 12. When the external tubing 11 needs to be separated from the monitor 12, the external tubing 11 and the monitor 12 may be separated from the connecting tube respectively.

Exemplarily, the external tubing 11 may have a first annular protrusion surrounding the first through hole 111, and the monitor 12 may have a second annular protrusion surrounding the second through hole 121. When the external tubing 11 is connected to the monitor 12, the first end of the connecting tube sleeves the first annular protrusion, the second end of the connecting tube sleeves the second annular protrusion, and the first through hole 111 is in communication with the through hole 121 by a tube body of the connecting tube.

Moreover, in the embodiment of the present disclosure, the shapes of the first annular protrusion and the second annular protrusion are not limited, as long as the first annular protrusion surrounds the first through hole 111 and the second annular protrusion surrounds the second through hole 121. For example, each of the shapes of the first annular protrusion and the second annular protrusion is a ring shape or a square ring shape. In one example, a sealing member 13 is the connecting tube.

In the embodiment of the present disclosure, a distance between the first annular protrusion and the first through hole 111, and a distance between the second annular protrusion and the second through hole 121 are not limited. Optionally, the distance between the first annular protrusion and the first through hole 111 and the distance between the second annular protrusion and the second through hole 121 may be both 1 to 3 millimeters (mm). In this way, the first through hole 111 is butt-jointed to and in communication with the second through hole 121 corresponding thereto more firmly.

Optionally, as shown in FIG. 2, FIG. 5, FIG. 10, FIG. 13 and FIG. 16, the respiratory monitor device further includes: the sealing member 13 as shown in the black filled pattern. The sealing member 13 is disposed between the external tubing 11 and the monitor 12. When the external tubing 11 is connected to the monitor 12, the connecting surface of the external tubing 11 and the connecting surface of the monitor 12 are sealed by the sealing member 13.

In this way, when the external tubing 11 is connected to the monitor 12, outside air can be prevented from entering the first through hole 111 and the second through hole 121, and the gas in the first through hole and the second through hole is also prevented from flowing out, thereby ensuring a monitoring accuracy of the respiratory monitor device.

In the embodiment of the present disclosure, a specific structure of the sealing member 13 is not limited, as long as the sealing member 13 can enable the first through hole 111 is butt-jointed to and in communication with the second through hole 121 corresponding thereto.

In the embodiment of the present disclosure, the position where the sealing member 13 is disposed is not limited, as long as the connecting surface of the external tubing 11 and the connecting surface of the monitor 12 can be sealed by the sealing member 13, such that the first through hole 111 is butt-jointed to and in communication with the second through hole 121 corresponding thereto without blocking the first through hole 111 and the second through hole 121. For example, the sealing member 13 is fixed on the external tubing 11 and/or the monitor 12.

In the embodiment of the present disclosure, a material of the sealing member 13 is not limited either, as long as when the sealing member 13 is subjected to an extrusion force applied by the external tubing 11 and the monitor 12, the extrusion force is greater than the pressure of an external medium where the sealing member 13 is disposed, such that the external tubing 11 is completely attached to the monitor 12 to achieve the butt-jointing and communication between the first through hole 111 and the second through hole 121 corresponding thereto.

Optionally, the sealing member 13 may be a structure which produces a sealing effect by the external extrusion force, or a fixed connection component with threads on the surface, or a structure achieving a connection effect by a magnetic attraction force. Exemplarily, the sealing member 13 is made of a deformable material. At this time, under the action of the extrusion force to the sealing member 13 applied by the external tubing 11 and the monitor 12, the sealing member 13 can seal the connecting surface of the external tubing 11 and the connecting surface of the monitor 12.

In the embodiment of the present disclosure, when the external tubing 11 and the monitor 12 are aligned, the external tubing 11 can be completely attached to the monitor 12 as long as the extrusion force applied to the sealing member 13 from the external tubing 11 and the monitor 12 is greater than the pressure of the external medium where the sealing member 13 is disposed. Therefore, the first through hole 111 is butt-jointed to and in communication with the second through hole 121 corresponding thereto, and the sealing is more efficient and more sanitary.

The following examples are taken to illustrate the practice of the sealing member 13.

Figure 3:
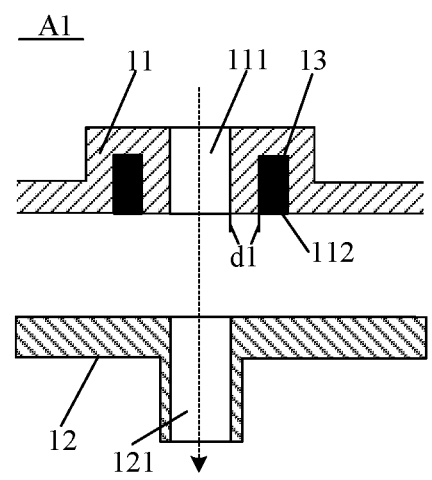
FIG. 3 is an enlarged view of area A1 in FIG. 2 in a separated state.
Figure 4:
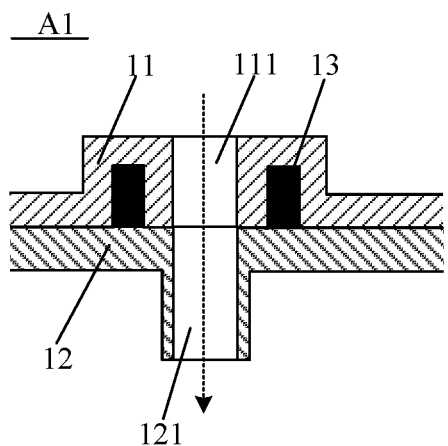
FIG. 4 is an enlarged view of area A1 in FIG. 2 in an aligned state.
Figure 5:
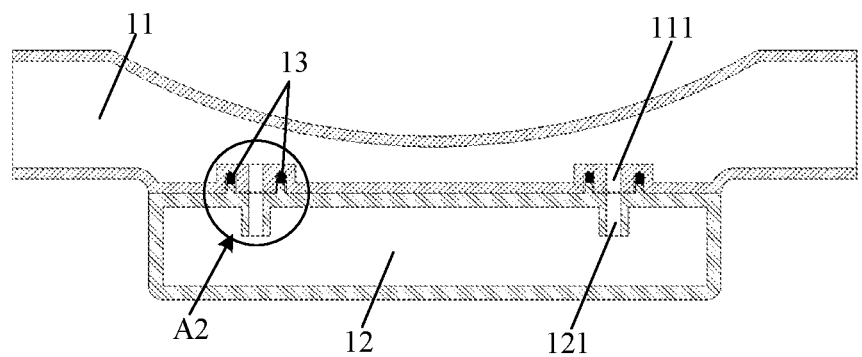
FIG. 5 is a schematic cross-sectional view of another respiratory monitor device according to an embodiment of the present disclosure.

In one example, as shown in FIG. 3 and FIG. 4, the connecting surface of the external tubing 11 is provided with a first annular slot 112 surrounding the first through hole 111. The sealing member 13 is embedded into the first annular slot 112. A thickness of the sealing member 13 is greater than or equal to a slot depth of the first annular slot 112. At this time, since the thickness of the sealing member 13 is greater than or equal to the slot depth of the first annular slot 112, when the monitor 12 and the external tubing 11 are aligned, the monitor 12 and the external tubing 11 extrude the sealing member 13, such that the connecting surface of the external tubing 11 and the connecting surface of the monitor 12 can be sealed by the sealing member 13. FIG. 3 and FIG. 4 are enlarged schematic diagrams of the structure inside circle A1 in FIG. 2. Moreover, when the thickness of the sealing member 13 is greater than the slot depth of the first annular slot 112, the sealing member 13 and the first annular slot 112 can achieve an interference fit, thereby effectively ensuring the sealing performance.

Figure 6:
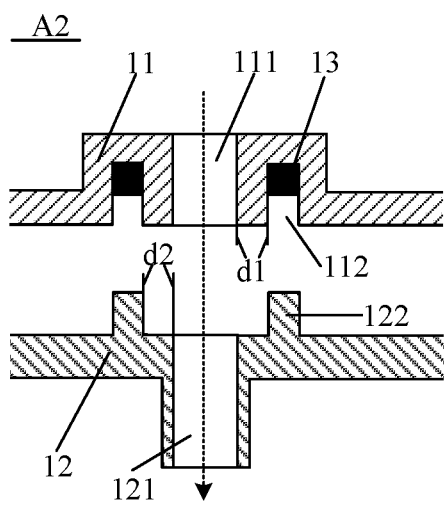
FIG. 6 is an enlarged view of area A2 in FIG. 5 in the separated state.
Figure 7:
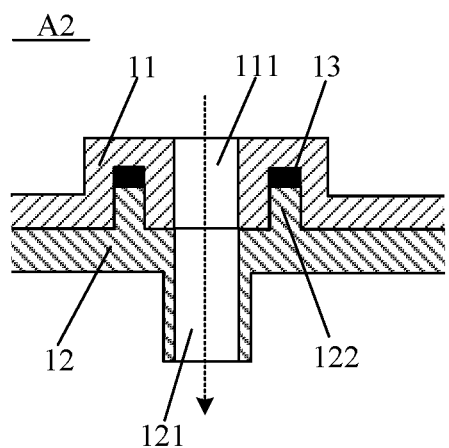
FIG. 7 is an enlarged view of area A2 in FIG. 5 in the aligned state.

Further, as shown in FIG. 6 and FIG. 7, when the first annular slot 112 surrounding the first through hole 111 is disposed in the connecting surface of the external tubing 11, and the sealing member 13 is embedded in the first annular slot 112, the connecting surface of the monitor 12 may be provided with a third annular protrusion 122 surrounding the second through hole 121. The third annular protrusion 122 matches the second annular slot in shape, and a sum of a height of the third annular protrusion 122 and the thickness of the sealing member 13 is greater than or equal to the slot depth of the first annular slot 112. At this time, since the sum of the height of the third annular protrusion 122 and the thickness of the sealing member 13 is greater than or equal to the slot depth of the first annular slot 112, when the monitor 12 and the external tubing 11 are aligned, the monitor 12 and the external tubing 11 extrude the sealing member 13, such that the connecting surface of the external tubing 11 and the connecting surface of the monitor 12 can be sealed by the sealing member 13. FIG. 6 and FIG. 7 are enlarged schematic diagrams of the structure inside the circle A2 in FIG. 5.

Figure 8:
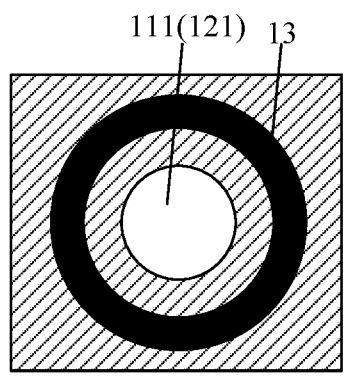
FIG. 8 is a schematic top view of an annular slot according to an embodiment of the present disclosure.
Figure 9:
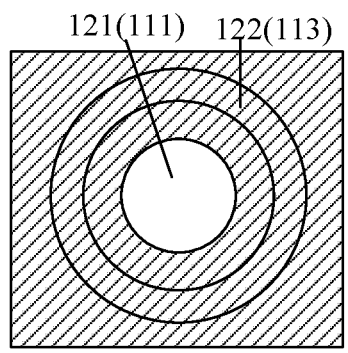
FIG. 9 is a schematic top view of an annular protrusion according to an embodiment of the present disclosure.
Figure 10:
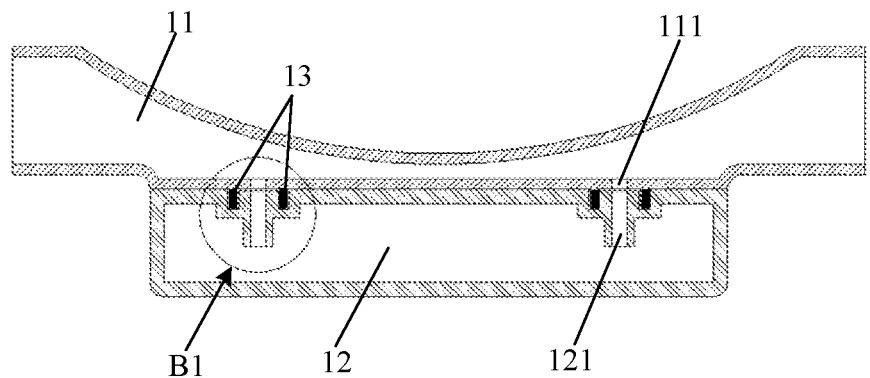
FIG. 10 is a schematic cross-sectional view of yet another respiratory monitor device according to an embodiment of the present disclosure.

In the embodiment of the present disclosure, the shapes of the first annular slot 112 and the third annular protrusion 122 are not limited, as long as the first annular slot 112 surrounds the first through hole 111 and the third annular protrusion 122 surrounds the second through hole 121. For example, as shown in FIG. 8, the shape of the first annular slot 112 may be a ring shape (the shape of the sealing member 13 in FIG. 8 is the shape of the first annular slot 112). As shown in FIG. 9, the third annular protrusion 122 may be a ring shape. Correspondingly, the sealing member 13 may be a ring-shaped sealing ring.

In the embodiment of the present disclosure, the distance d1 between the first annular slot 112 and the first through hole 111, and the distance d2 between the third annular protrusion 122 and the second through hole 121 are not limited. Optionally, the distance d1 between the first annular slot 112 and the first through hole 111 and the distance d2 between the third annular protrusion 122 and the second through hole 121 are both 1 to 3 mm. In this way, the first through hole 111 is butt-jointed to and in communication with the second through hole 121 corresponding thereto more firmly.

In the embodiment of the present disclosure, the sealing member 13 is embedded in the first annular slot 112. When the monitor 12 and the external tubing 11 are aligned, the third annular protrusion 122 and the first annular slot 112 simultaneously apply the extrusion force to the sealing member 13. Therefore, the external tubing 11 and the monitor 12 are completely attached, such that the connecting surface of the external tubing 11 and the connecting surface of the monitor 12 are sealed by the sealing member 13.

The sealing member 13 may also be embedded into the first annular slot 112 and sleeve the third annular protrusion 122, which is not specifically limited in the embodiment of the present disclosure.

Figure 11:
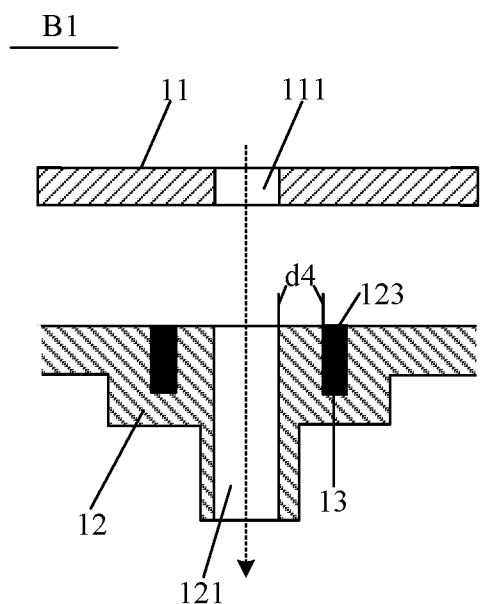
FIG. 11 is an enlarged view of area B1 in FIG. 10 in the separated state.
Figure 12:
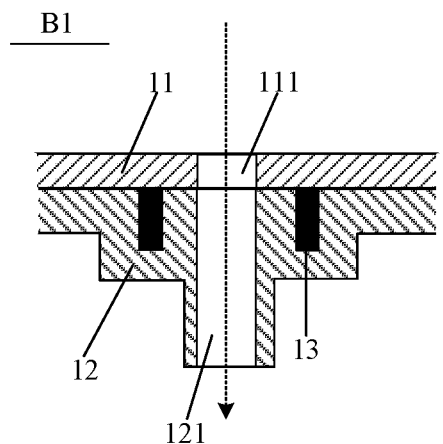
FIG. 12 is an enlarged view of area B1 in FIG. 10 in the aligned state.
Figure 13:
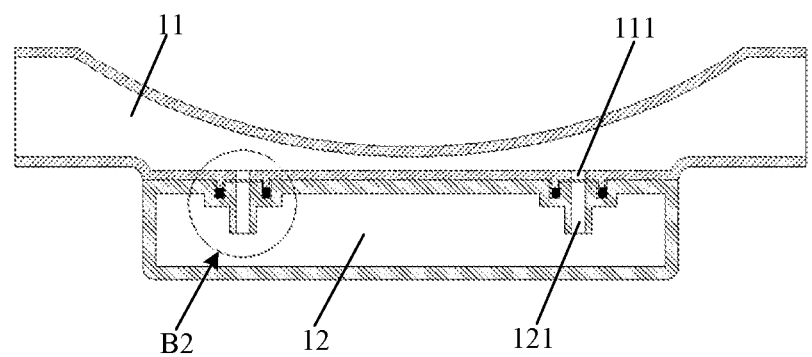
FIG. 13 is a schematic cross-sectional view of still a further respiratory monitor device according to an embodiment of the present disclosure.

In another example, as shown in FIG. 11 and FIG. 12, the connecting surface of the monitor 12 is provided with a second annular slot 123 surrounding the second through hole 121, and the sealing member 13 is embedded into the second annular slot 123. The thickness of the sealing member 13 is greater than or equal to the slot depth of the second annular slot 123. At this time, since the thickness of the sealing member 13 is greater than or equal to the depth of the second annular slot 123, when the monitor 12 and the external tubing 11 are aligned, the monitor 12 and the external tubing 11 extrude the sealing member 13, such that the connecting surface of the external tubing 11 and the connecting surface of the monitor 12 can be sealed by the sealing member. FIG. 11 and FIG. 12 are enlarged schematic diagrams of the structure inside the circle B1 in FIG. 10.

Figure 14:
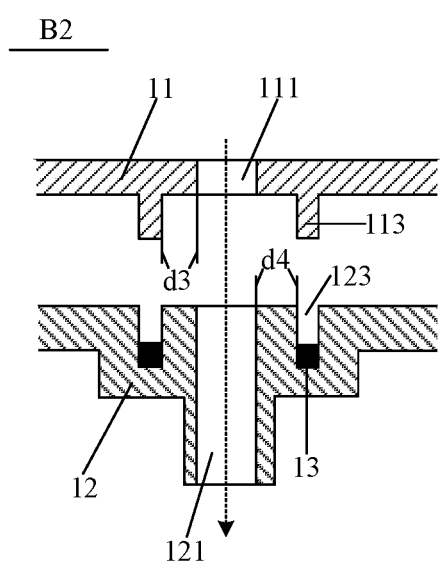
FIG. 14 is an enlarged view of area B2 in FIG. 13 in the separated state.
Figure 15:
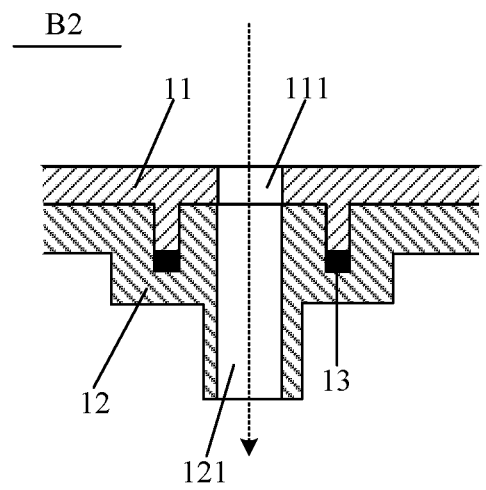
FIG. 15 is an enlarged view of area B2 in FIG. 13 in the aligned state.
Figure 16:
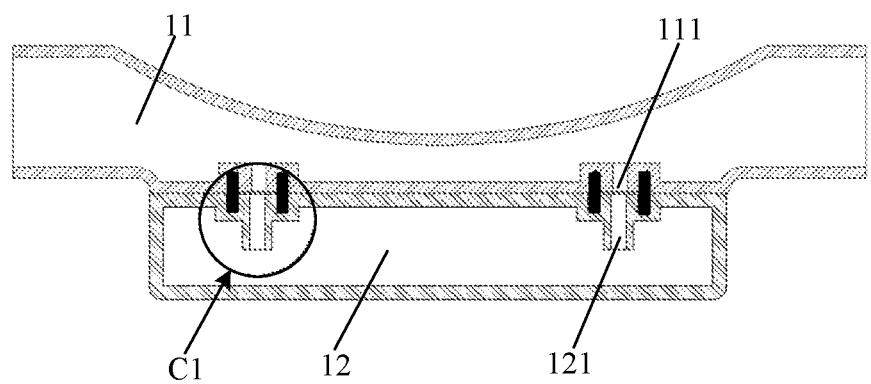
FIG. 16 is a schematic cross-sectional view of one additional respiratory monitor device according to an embodiment of the present disclosure.

Further, as shown in FIG. 14 and FIG. 15, when the second annular slot 123 surrounding the second through hole 121 is disposed in the connecting surface of the monitor 12, and the sealing member 13 is embedded into the second annular slot 123, the connecting surface of the external tubing 11 is provided with a fourth annular protrusion 113 surrounding the first through hole 111. The fourth annular protrusion 113 matches the second annular slot 123 in shape. A sum of a height of the fourth annular protrusion 113 and the thickness of the sealing member 13 is greater than or equal to the slot depth of the second annular slot 123. At this time, since the sum of the height of the fourth annular protrusion 113 and the thickness of the sealing member 13 is greater than or equal to the depth of the second annular slot 123, when the monitor 12 and the external tubing are aligned, the monitor 12 and the external tubing 11 extrude the sealing member 13, such that the connecting surface of the external tubing 11 and the connecting surface of the monitor 12 can be sealed by the sealing member 13. FIG. 14 and FIG. 15 are enlarged schematic diagrams of the structure inside the circle B2 in FIG. 13.

In the embodiments of the present disclosure, the shapes of the fourth annular protrusion 113 and the second annular slot 123 are not limited, as long as the fourth annular protrusion 113 surrounds the first through hole 111 and the second annular slot 123 surrounds the second through hole 121. For example, as shown in FIG. 9, the shape of the fourth annular protrusion 113 may be a ring shape. As shown in FIG. 8, the shape of the second annular slot 123 may be a ring shape (the shape of the sealing member 13 in FIG. 8 is the shape of the second annular slot 123). Correspondingly, the sealing member 13 may be a ring-shaped sealing ring.

In the embodiment of the present disclosure, the distance d3 between the fourth annular protrusion 113 and the first through hole 111, and the distance d4 between the second annular slot 123 and the second through hole 121 are not limited. Optionally, the distance d3 between the fourth annular protrusion 113 and the first through hole 111 and the distance d4 between the second annular slot 123 and the second through hole 121 are both 1 to 3 mm. In this way, the first through hole 111 is butt-jointed to and in communication with the second through hole 121 corresponding thereto more firmly.

In the embodiment of the present disclosure, the sealing member 13 is embedded in the second annular slot 123. When the monitor 12 and the external tubing 11 are aligned, the fourth annular protrusion 113 and the second annular slot 123 simultaneously apply the extrusion force to the sealing member 13. Therefore, the external tubing 11 is completely attached to the monitor 12 to achieve a sealed connection between the first through hole 111 and the second through hole 121 corresponding thereto.

The sealing member 13 may be embedded in the second annular slot 123 and also sleeve the fourth annular protrusion 113, which is not specifically limited in the embodiment of the present disclosure.

Figure 17:
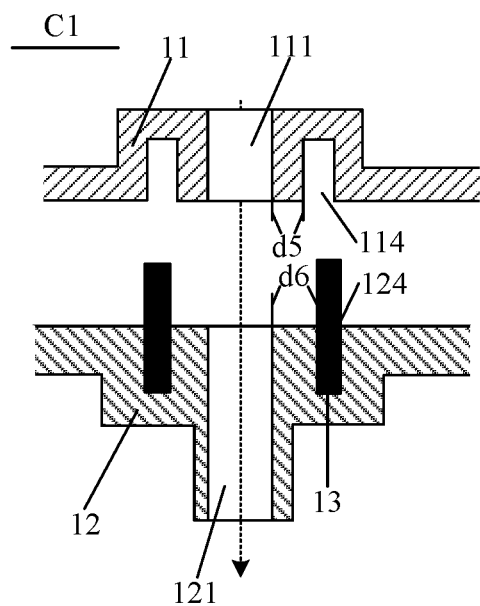
FIG. 17 is an enlarged view of area C1 in FIG. 16 in the separated state.
Figure 18:
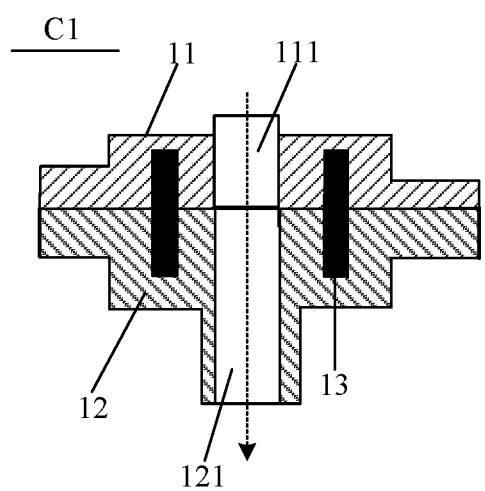
FIG. 18 is an enlarged view of area C1 in FIG. 16 in the aligned state.

In still another example, as shown in FIG. 17 and FIG. 18, the connecting surface of the monitor 12 is provided with a third annular slot 124 surrounding the second through hole 121. The connecting surface of the external tubing 11 is provided a fourth annular slot 114 surrounding the first through hole 111. The sealing member 13 is embedded into at least one of the third annular slot 124 and the fourth annular slot 114, and the thickness of the sealing member 13 is greater than or equal to the sum of the slot depths of the third annular slot 124 and the fourth annular slot 114. At this time, since the thickness of the sealing member 13 is greater than or equal to the sum of the slot depths of the third annular slot 124 and the fourth annular slot 114, when the monitor 12 and the external tubing 11 are aligned, the external tubing 11 and the monitor 12 simultaneously extrude the sealing member 13, such that the connecting surface of the external tubing 11 and the connecting surface of the monitor 12 can be sealed by the sealing member 13. FIG. 17 and FIG. 18 are enlarged schematic diagrams of the structure inside the circle C1 in FIG. 16.

In the embodiment of the present disclosure, the shapes of the third annular slot 124 and the fourth annular slot 114 are not limited, as long as the fourth annular slot 114 surrounds the first through hole 111 and the third annular slot 124 surrounds the second through hole. 121. Exemplarily, the shapes of the third annular slot 124 and the fourth annular slot 114 are both a ring shape. Correspondingly, the sealing member 13 may be a ring-shaped sealing ring.

In the embodiment of the present disclosure, the distance d5 between the fourth annular slot 114 and the first through hole 111, and the distance d6 between the third annular slot 124 and the second through hole 121 are not limited. Optionally, the distance d5 between the fourth annular slot 114 and the first through hole 111 and the distance d6 between the third annular slot 124 and the second through hole 121 are both 1 to 3 mm. In this way, the first through hole 111 is butt-jointed to and in communication with the second through hole 121 corresponding thereto more firmly.

Optionally, as shown in FIG. 1, the plurality of first through holes 111 are arranged in sequence along a direction from the gas inlet to the gas outlet. Correspondingly, the plurality of second through holes 121 are also arranged in sequence along the direction from the gas inlet to the gas outlet. That is, the plurality of first through holes 111 and the plurality of second through holes 121 are arranged in sequence along a gas flow path. In this way, the monitor 12 can detect the gas flow at different positions on the gas flow path, thereby effectively ensuring the detection accuracy.

In the embodiment of the present disclosure, the monitor 12 is configured to detect a pressure difference of the gas based on the flow direction of the gas, so as to measure a flow rate of the gas. In one example, the monitor 12 may also include a pressure sensor and a differential pressure sensor. The gas flowing into the monitor 12 from the first through hole 111 flows to the pressure sensor and the differential pressure sensor by the second through hole 121. The differential pressure sensor measures the pressure difference of the gas based on the received gas, and the pressure sensor measures a pressure intensity of the gas based on the received gas. Based on the pressure difference and the pressure intensity, the flow rate of the gas circulating in the external tubing can be calculated to realize the monitoring of the flow rate of the gas circulating in the external tubing. When the gas circulating in the external tubing is the gas input to the user, by monitoring the flow rate of the gas, it can be ensured that the gas flow rate inhaled by the user is within a reasonable range. When the gas circulating in the external tubing is the gas exhaled by the user, the respiration of the user can be monitored by monitoring the flow rate of the gas.

Optionally, as shown in FIG. 1, the number of second through holes 121 may be three. The monitor 12 includes at least one pressure sensor and at least one differential pressure sensor. In the at least three second through holes 121, certain ends of two adjacent second through holes 121 going distally from the external tubing 11 are both in direct contact with the differential pressure sensor, and one end of any one second through hole 121 of the remaining second through holes 121 going distally from the external tubing 11 is in direct contact with the pressure sensor. The differential pressure sensor is configured to acquire the difference of the pressure intensities of the gas entering the monitor 12 from the two adjacent second through holes 121. The pressure sensor is configured to acquire the pressure intensity of the gas entering the monitor 12 from any one second through hole 121 of the remaining second through holes 121.

When the gas flows in the direction from the gas inlet to the gas outlet, a part of the gas may flow into the monitor 12 through the first through hole 111. Therefore, the plurality of second through holes 121 are arranged in sequence along the direction from the gas inlet to the gas outlet. Besides, certain ends of two adjacent second through holes 121 going distally from the external tubing 11 are in direct contact with the differential pressure sensor. The pressure difference of the gas from the two adjacent second through holes 121 to the differential pressure sensor can be measured, and the flow rate of the gas is calculated based on the pressure difference, thereby ensuring that the flow rate of the gas inhaled by the user is within a reasonable range.

Alternatively, when the gas exhaled by the user flows in the direction from the gas outlet to the gas inlet, a part of the gas may flow into the monitor 12 through the first through hole 111. Therefore, the plurality of second through holes 121 are arranged in sequence along the direction from the gas inlet to the gas outlet, and certain ends of two adjacent second through holes 121 going distally from the external tubing 11 are in direct contact with the differential pressure sensor. The pressure difference of the gas exhaled by the user from the two adjacent second through holes 121 to the differential pressure sensor can be measured. Besides, the flow rate of the gas exhaled by the user is calculated based on the pressure difference, so as to monitor the respiratory condition of the user.

In the embodiment of the present disclosure, the second through hole 121 in direct contact with the pressure sensor may be disposed in one side, close to the gas inlet, of the two adjacent second through holes 121 in direct contact with the differential pressure sensor. Or, the second through hole 121 in direct contact with the pressure sensor may be disposed in one side, close to the gas outlet, of the two adjacent second through holes 121 in direct contact with the differential pressure sensor.

In the embodiment of the present disclosure, by disposing the second through hole 121 for transmitting the gas to the pressure sensor and the differential pressure sensor in the monitor 12, on the basis of realizing the respiratory monitoring function, the gas flow rate at the gas outlet is not affected, and a gas supply of the respiratory monitor device is saved.

Figure 19:
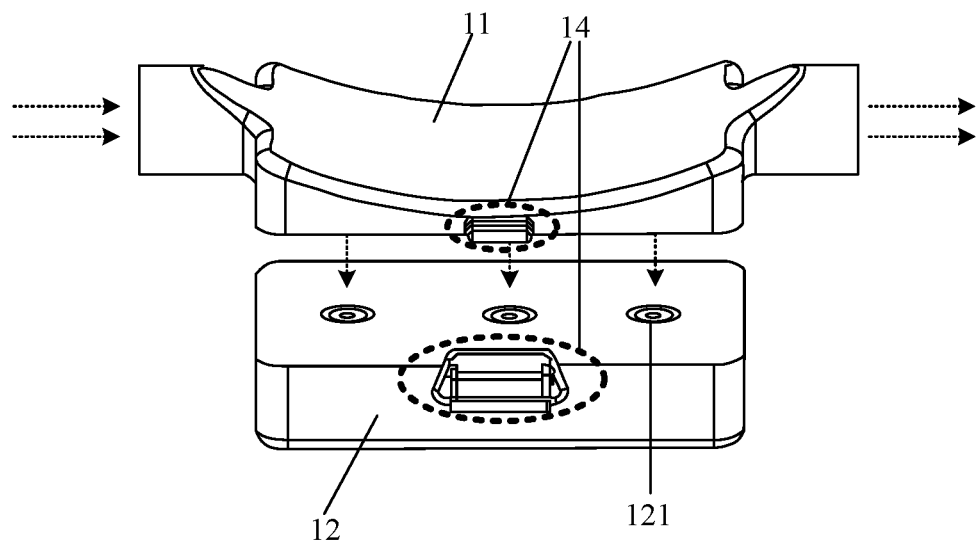
FIG. 19 is a schematic structural diagram of one more respiratory monitor device according to an embodiment of the present disclosure.

Optionally, as shown in FIG. 19, the respiratory monitor device further includes a locking switch 14. The locking switch 14 is configured to fixedly connect the monitor 12 and the external tubing 11. That is, when the locking switch 14 is in a locked state, the locking switch 14 is configured to fixedly connect the monitor 12 and the external tubing 22. When the locking switch 14 is in an unlocked state, the monitor 12 can be separated from the external tubing.

In the embodiment of the present disclosure, the locking switch 14 may be disposed on an inner side surface or outer side surface of the respiratory monitor device. Moreover, in the case where the locking switch 14 is disposed on the inner side surface of the respiratory monitor device, a trigger switch may be disposed on the outer side surface of the respiratory monitor device, such that the state of the locking switch 14 is controlled by using the trigger switch. Alternatively, a communicative connection between the respiratory monitor device and a mobile terminal may be established, and the trigger switch is disposed on the mobile terminal, such that the state of the locking switch 14 is controlled by the trigger switch. Exemplarily, the mobile terminal may be a mobile phone. For example, the trigger switch may be a touch switch.

In the embodiment of the present disclosure, the structure of the locking switch 14 is not limited, as long as the locking switch 14 can enable the external tubing 11 and the monitor 12 to be fixedly connected. For example, the locking switch 14 may be one of a snap switch and an electromagnetic switch. The locking switch 14 may also have other structures, which is not specifically limited in the embodiment of the present disclosure.

In the embodiment of the present disclosure, the locking switch 14 is configured to fixedly connect the monitor 12 and the external tubing 11 or separate the monitor 12 from the external tubing 11. Meanwhile, if the first through hole 111 and the second through hole 121 corresponding thereto are hermetically connected based on the extrusion force applied to the sealing member 13 from the external tubing 11 and the monitor 12, the locking switch 14 is configured to fixedly connect the monitor 12 and the external tubing 11, which is equivalent to applying the extrusion force to the sealing member 13. Therefore, the first through hole 111 and the second through hole 121 corresponding thereto are hermetically connected through the sealing member 13. The locking switch 14 is unlocked, which is equivalent to removing the extrusion force applied to the sealing member 13, the monitor 12 is separated from the external tubing 11, and the first through hole 111 is separated from the second through hole 121 corresponding thereto.

In summary, in the respiratory monitor device according to the embodiment of the present disclosure, since the monitor is detachably connected to the external tubing, when the external tubing needs to be cleaned, the external tubing can be detached from the respiratory monitor device, and the external tubing is cleaned separately to avoid damage to the monitor during cleaning since the external tubing and the monitor are non-removable.

Figure 20:
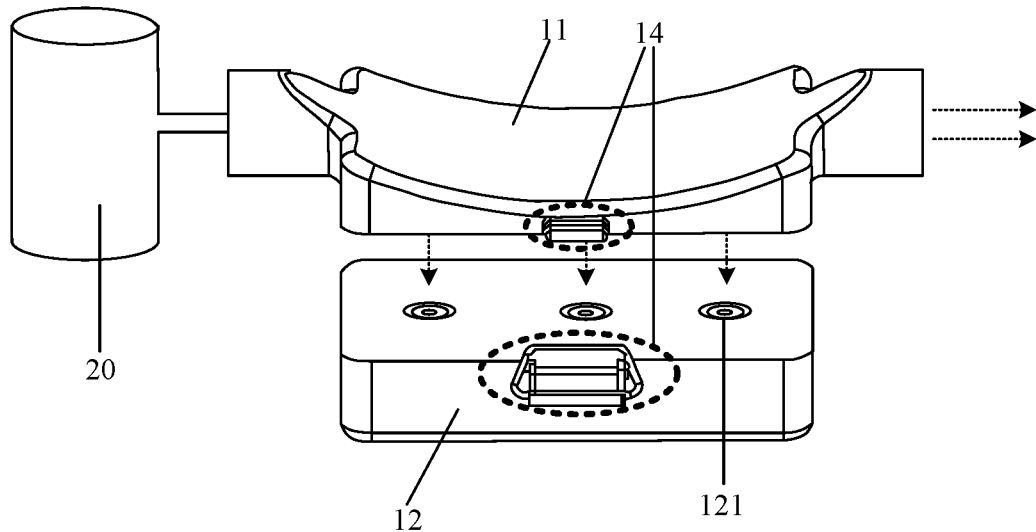
FIG. 20 is a schematic structural diagram of a respiratory monitoring system according to an embodiment of the present disclosure.

The embodiment of the present disclosure also provides a respiratory monitoring system, which, as shown in FIG. 20, includes an oxygen generator 20 and the respiratory monitor device according to the embodiment of the present disclosure. An oxygen outlet of the oxygen generator 20 may be fixedly connected to the gas inlet of the respiratory monitor device.

The embodiment of the present disclosure provides the respiratory monitoring system, including the oxygen generator 20 and the respiratory monitor device according to the embodiment of the present disclosure. The oxygen generator 20 is configured to deliver oxygen to the respiratory monitor device so as to provide oxygen to the user. The respiratory monitor device is configured to hermetically connect the first through hole 111 and the second through hole 121 corresponding thereto by using the sealing member 13 when the external tubing 11 and the monitor 12 are aligned. Outside air is prevented from entering the first through hole 111 and the second through hole 121, and the gas in the first through hole 111 and the second through hole 121 is also prevented from flowing out, thereby avoiding the impact on the accuracy of the respiratory monitor device. Meanwhile, as long as the sealing member 13 is loosened, the external tubing 11 can be separated from the monitor 12, such that the external tubing 11 is cleaned separately.

It should be noted that in the accompanying drawings, for clarity of the illustration, the dimension of the layers and areas may be scaled up. It may be understood that when a member or layer is described as being "above" another member or layer, the described member or layer may be directly on the other member or layer, or at least one intermediate layer may be arranged between the described member or layer and the other member or layer. In addition, it may be understood that when a member or layer is described as being "below" another member or layer, the described member or layer may be directly below the other member or layer, or at least one intermediate layer may be arranged between the described member or layer and the other member or layer. In addition, it may be further understood that when a layer or member is described as being arranged "between" two layers or members, the described layer or member may be the only layer between the two layers or members, or at least one intermediate layer or member may be arranged between the described member or layer and the two layers or members. In the whole description described above, like reference numerals denote like members.

In the present disclosure, the terms "first" and "second" are used for descriptive purposes only and are not to be construed as indicating or implying relative importance. The term "a plurality of" refers to two or more, unless specifically defined otherwise.

Apparently, the above embodiments of the present disclosure are merely examples to clearly illustrate the present disclosure, but are not intended to limit the practice of the present disclosure. For those of ordinary skilled in the art, other different forms of changes or alterations can also be made on the basis of the foregoing description, and it is not possible to list all the embodiments herein. Any obvious changes or alterations derived from the technical solutions of the present disclosure are still within the scope of protection of the present disclosure.

What is claimed is:

1. A respiratory monitor device, comprising an external tubing and a monitor, wherein the external tubing and the monitor are detachably connected;
    the external tubing is provided with a gas inlet and a gas outlet, the gas inlet being in communication with the gas outlet by a chamber of the external tubing; and the external tubing comprises a plurality of first through holes; and
    the monitor comprises a plurality of second through holes, wherein when the external tubing is connected to the monitor, the plurality of first through holes are in communication with the plurality of second through holes in one-to-one correspondence, and the monitor is configured to detect gas entering the monitor from the second through holes;
    the external tubing and the monitor are each provided with a connecting surface, wherein one of the connecting surface of the external tubing and the connecting surface of the monitor is provided with a plurality of clamping slots, the other of the connecting surface of the external tubing and the connecting surface of the monitor is provided with a plurality of protrusions matching the plurality of clamping slots,
    wherein each of the plurality of the clamping slots surrounds a respective one of the plurality of first through holes or the plurality of second through holes, a respective one of a plurality of sealing members is embedded in a respective one of the plurality of clamping slots, and a thickness of the respective one of the plurality of sealing members is less than a slot depth of the respective one of the plurality of clamping slots; wherein a height of a respective one of the plurality of protrusions is greater than the thickness of the respective one of the plurality of sealing members, and a sum of the height of the respective one of the plurality of protrusions and the thickness of the respective one of the plurality of sealing members is greater than or equal to the slot depth of the respective one of the plurality of clamping slots.

2. The respiratory monitor device according to claim 1, wherein each of the plurality of clamping slots is a rectangular slot, and each of the plurality of protrusions is a rectangular protrusion.

3. The respiratory monitor device according to claim 1, wherein each of the plurality of clamping slots is a circular slot, and each of the plurality of protrusions is a circular protrusion.

4. The respiratory monitor device according to claim 1, wherein the plurality of first through holes and the plurality of second through holes are connected by a pluggable connecting tube.

5. The respiratory monitor device according to claim 4, wherein the external tubing is provided with a first annular protrusion surrounding the respective one of the plurality of first through holes and the monitor is provided with a second annular protrusion surrounding the respective one of the plurality of second through holes, wherein when the external tubing is connected to the monitor, a first end of the connecting tube sleeves the first annular protrusion, a second end of the connecting tube sleeves the second annular protrusion, and the respective one of the plurality of first through holes is in communication with the respective one of the plurality of second through holes by a tube body of the connecting tube.

6. The respiratory monitor device according to claim 1, wherein a first annular slot surrounding the respective one of the plurality of first through holes is disposed in the connecting surface of the external tubing, wherein the first annular slot is one of the plurality of clamping slots, and the respective one of the plurality of sealing members is embedded in the first annular slot; and
    the connecting surface of the monitor is provided with a third annular protrusion surrounding the respective one of the plurality of second through holes, wherein the third annular protrusion is one of the plurality of protrusions, the third annular protrusion matches the first annular slot in shape, and a sum of a height of the third annular protrusion and a thickness of the respective one of the plurality of sealing members is greater than or equal to a slot depth of the first annular slot.

7. The respiratory monitor device according to claim 1, wherein a second annular slot surrounding the respective one of the plurality of second through holes is disposed in the connecting surface of the monitor, wherein the second annular slot is one of the plurality of clamping slots, and the respective one of the plurality of sealing members is embedded in the second annular slot; and a fourth annular protrusion surrounding the respective one of the plurality of first through holes is disposed on the connecting surface of the external tubing, wherein the fourth annular protrusion is one of the plurality of protrusions, the fourth annular protrusion matches the second annular slot in shape, and a sum of a height of the fourth annular protrusion and a thickness of the respective one of the plurality of sealing members is greater than or equal to a slot depth of the second annular slot.

8. The respiratory monitor device according to claim 1, wherein the sealing member is made of a deformable material.

9. The respiratory monitor device according to claim 1, wherein the sealing member is a sealing ring.

10. The respiratory monitor device according to claim 1, wherein the plurality of first through holes are sequentially arranged along a direction from the gas inlet to the gas outlet.

11. The respiratory monitor device according to claim 10, wherein the plurality of second through holes is at least three;
the monitor comprises at least one pressure sensor and at least one differential pressure sensor; wherein in the at least three second through holes, one end of at least one pair of two adjacent second through holes going distally from the external tubing is in direct contact with the differential pressure sensor, the differential pressure sensor is configured to acquire a difference between pressure intensities of the gas entering the monitor from the two adjacent second through holes, one end of at least one remaining second through hole going distally from the external tubing is in direct contact with one of the pressure sensors, and the pressure sensor is configured to acquire the pressure intensity of the gas entering the monitor from the one end of the at least one remaining second through hole.

12. The respiratory monitor device according to claim 1, further comprising a locking switch, wherein the locking switch is configured to fixedly connect the monitor and the external tubing.

13. The respiratory monitor device according to claim 12, wherein the locking switch is one of a snap switch and an electromagnetic switch.

14. A respiratory monitoring system, comprising an oxygen generator and a respiratory monitor device; wherein
the respiratory monitor device comprises an external tubing and a monitor, wherein the external tubing and the monitor are detachably connected;
the external tubing is provided with a gas inlet and a gas outlet, the gas inlet being in communication with the gas outlet by a chamber of the external tubing; and the external tubing comprises a plurality of first through holes; and
the monitor comprises a plurality of second through holes, wherein when the external tubing is connected to the monitor, the plurality of first through holes are in communication with the plurality of second through holes in one-to-one correspondence, and the monitor is configured to detect gas entering the monitor from the second through holes;
the external tubing and the monitor are each provided with a connecting surface, wherein one of the connecting surface of the external tubing and the connecting surface of the monitor is provided with a plurality of clamping slots, the other of the connecting surface of the external tubing and the connecting surface of the monitor is provided with a plurality of protrusions matching the plurality of clamping slots,
wherein each of the plurality of the clamping slots surrounds a respective one of the plurality of first through holes or the plurality of second through holes, a respective one of a plurality of sealing members is embedded in a respective one of the plurality of clamping slots, and a thickness of the respective one of the plurality of sealing members is less than a slot depth of the respective one of the plurality of clamping slots; wherein a height of a respective one of the plurality of protrusions is greater than the thickness of the respective one of the plurality of sealing members, and a sum of the height of the respective one of the plurality of protrusions and the thickness of the respective one of the plurality of sealing members is greater than or equal to the slot depth of the respective one of the plurality of clamping slots; and
an oxygen outlet of the oxygen generator is configured to be fixedly connected to the gas inlet of the respiratory monitor device.

\* \* \* \* \*